(12) United States Patent
Phillips et al.

(10) Patent No.: US 9,044,268 B2
(45) Date of Patent: Jun. 2, 2015

(54) METHOD OF IDENTIFYING THE ORIENTATION OF A TISSUE SAMPLE

(76) Inventors: Michael Phillips, Oconomowoc, WI (US); Janet Phillips, Oconomowoc, WI (US)

( * ) Notice: Subject to any disclaimer, the term of this patent is extended or adjusted under 35 U.S.C. 154(b) by 978 days.

(21) Appl. No.: 13/097,329

(22) Filed: Apr. 29, 2011

(65) Prior Publication Data

US 2011/0212253 A1     Sep. 1, 2011

Related U.S. Application Data

(60) Division of application No. 11/873,249, filed on Oct. 16, 2007, now abandoned, which is a continuation-in-part of application No. 10/978,948, filed on Nov. 1, 2004, now abandoned.

(51) Int. Cl.
    *G01N 1/00*     (2006.01)
    *A61B 19/00*     (2006.01)

(52) U.S. Cl.
    CPC ......... *A61B 19/54* (2013.01); *A61B 2019/5408* (2013.01); *A61B 2019/545* (2013.01)

(58) Field of Classification Search
    CPC ..... A61B 19/54; A61B 2019/508; G01N 1/00
    See application file for complete search history.

(56) References Cited

U.S. PATENT DOCUMENTS

| | | |
|---|---|---|
| 2,138,241 A | 11/1938 | Koch et at |
| 2,297,990 A | 10/1942 | Schmitt et at |
| 2,643,765 A * | 6/1953 | Bradshaw .................... 206/63.3 |
| 2,738,606 A | 3/1956 | Klein |
| 2,932,906 A | 4/1960 | Chamberlain |
| 3,352,280 A | 11/1967 | Hughes et al. |
| 3,635,808 A | 1/1972 | Elevitch |
| 4,025,393 A | 5/1977 | Hirschfeld |
| 4,034,700 A | 7/1977 | Bassett et al. |
| 4,510,119 A | 4/1985 | Hevey |
| 4,584,042 A | 4/1986 | Wandroik |
| 4,681,471 A | 7/1987 | Hayduchok et al. |
| 4,739,906 A | 4/1988 | LoTurco |
| 5,092,184 A | 3/1992 | Goodell et al. |
| 5,098,661 A | 3/1992 | Froehlich et al. |
| 5,670,118 A | 9/1997 | Sponholtz |
| 5,743,899 A | 4/1998 | Zinreich |
| 5,865,305 A | 2/1999 | Yasoshima |

(Continued)

FOREIGN PATENT DOCUMENTS

| | | |
|---|---|---|
| DE | 3445085 | 2/1987 |
| DE | 10220238 A1 | 1/2004 |
| JP | 03051200 A | 3/1991 |

OTHER PUBLICATIONS

About Rubber Stamps.com; Rubber Stamps and rubber stamp accessories from Inkadinkado; Colorbox Ink Pads—3 colors; website: www.aboutrubberstamps.com/colorbox3colors.html; Sep. 27, 2004, 1 page.

*Primary Examiner* — Jyoti Nagpaul
(74) *Attorney, Agent, or Firm* — Barbara A. Wrigley; Oppenheimer Wolff & Donnelly LLP

(57) ABSTRACT

A method of identifying the orientation of a tissue sample is provided. The method includes the use of a single-use tissue marking system for use in marking a tissue sample. A first surface of the sample is marked with a first ink defined by a first color; a second surface of the tissue is marked with a second ink defined by a second color; and a third surface of the sample is marked with a third ink defined by a third color.

11 Claims, 6 Drawing Sheets

(56) References Cited

U.S. PATENT DOCUMENTS

| | | | |
|---|---|---|---|
| 5,895,762 A | 4/1999 | Greenfield et al. | |
| 5,927,009 A | 7/1999 | Vanwingerden | |
| 5,955,352 A | 9/1999 | Inoue et al. | |
| 5,958,341 A | 9/1999 | Chu | |
| 6,197,034 B1 | 3/2001 | Gvozdic et al. | |
| 6,254,826 B1 | 7/2001 | Acosta et al. | |
| 6,286,682 B1 | 9/2001 | d'Arbelles | |
| 6,321,487 B1 | 11/2001 | Sardanelli et al. | |
| 6,372,313 B1 | 4/2002 | D'Alessio et al. | |
| 6,372,895 B1 | 4/2002 | Bentsen et al. | |
| 6,464,506 B1 | 10/2002 | Welles | |
| 6,569,676 B1 | 5/2003 | Tripp et al. | |
| 6,703,247 B1 | 3/2004 | Chu | |
| 6,723,290 B1 | 4/2004 | Wardlaw | |
| 6,725,802 B1 | 4/2004 | Carrington et al. | |
| 6,740,068 B1 | 5/2004 | Arruffoo et al. | |
| 6,743,228 B2 | 6/2004 | Lee et al. | |
| 6,945,017 B1 | 9/2005 | Bonney et al. | |
| 7,870,951 B1 | 1/2011 | Orsi | |
| 2001/0025579 A1 | 10/2001 | Winston | |
| 2002/0081328 A1* | 6/2002 | Brooks et al. | 424/449 |
| 2003/0220640 A1 | 11/2003 | Lee et al. | |
| 2005/0234322 A1 | 10/2005 | Lober | |

\* cited by examiner

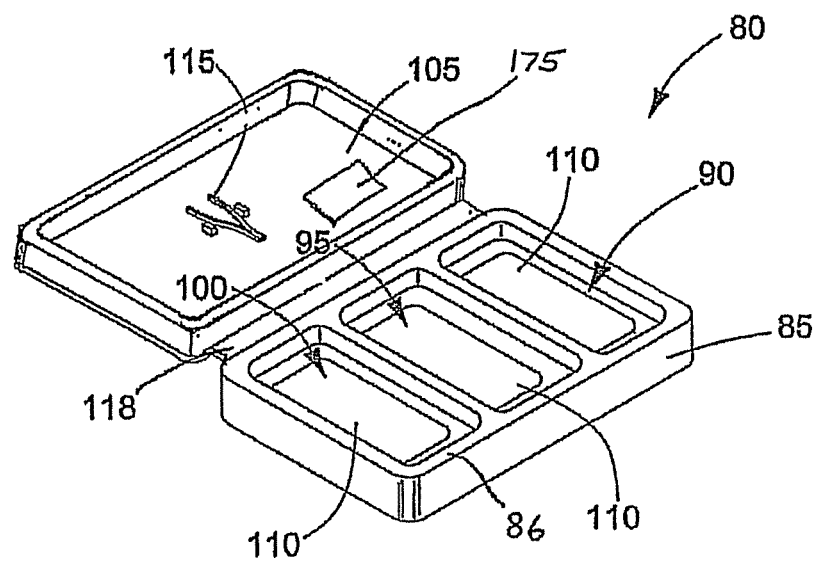
FIG. 5
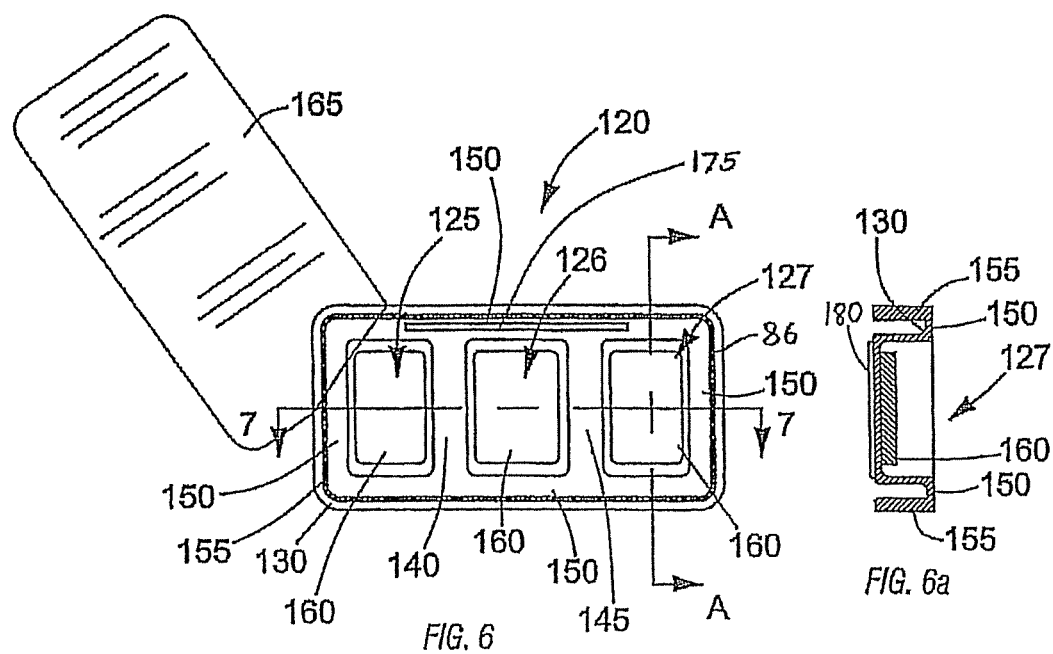
FIG. 6
FIG. 6a

METHOD OF IDENTIFYING THE ORIENTATION OF A TISSUE SAMPLE

RELATED APPLICATION DATA

This application is a divisional of U.S. patent application Ser. No. 11/873,249, filed Oct. 16, 2007; which is a continuation-in-part of U.S. patent application Ser. No. 10/978,948, filed Nov. 1, 2004 (now abandoned), which is fully incorporated herein by reference.

BACKGROUND OF THE INVENTION

The present invention relates to a tissue marking system. More particularly, the present invention relates to a tissue marking system that includes ink.

During surgery, it is often necessary to remove a sample of tissue and closely examine that tissue sample while knowing its original orientation within the patient. For example, cancerous tumors are often removed from the patient and then examined to verify that a sufficient margin of tissue surrounding the tumor has been removed. To determine this, the tissue sample is examined and the margins on each surface are identified. Should a margin be insufficient, it is important for the surgeon to know the orientation of the sample to allow for the removal of additional tissue in the proper area.

Presently, different color sutures, different length sutures, or different quantities of sutures are inserted into the tissue sample to identify the orientation of the tissue. However, this is time consuming and the sutures can be accidentally removed making identification of the tissue orientation difficult.

BRIEF SUMMARY OF THE INVENTION

In one construction, the invention provides a single-use tissue marking system for use in marking a tissue sample. The system includes a container and a first number of ink reservoirs at least partially defined by the container. Each reservoir contains ink of a different color. The system also includes a second number of applicators. Each applicator is configured to absorb a quantity of ink for application to the tissue sample. A cover is coupled to and cooperates with the container to fully enclose each of the first number of ink reservoirs.

In another construction, the invention provides a tissue marking system that includes a first ink reservoir containing ink of a first color, a second ink reservoir containing ink of a second color different from the first color, and a first isolation space positioned between the first ink reservoir and the second ink reservoir. A third ink reservoir contains ink of a third color different from the first color and the second color and a second isolation space is positioned between the second ink reservoir and the third ink reservoir. A one piece cover is in sealable contact with the first isolation space and the second isolation space to sealably separate the first ink reservoir, the second ink reservoir, and the third ink reservoir. The cover is configured to be removed as one piece to expose each of the first ink reservoir, the second ink reservoir, and the third ink reservoir.

In yet another construction, the invention provides a tissue marking system for use in marking a tissue sample. The system includes a container defining a space and six ink reservoirs at least partially defined by the container. Each reservoir contains ink of a different color. Six applicators are disposed within the space. Each applicator is configured to absorb a quantity of ink for application to the tissue sample. A fixative is disposed within the space and a single cover is coupled to the container to fully enclose each of the six ink reservoirs and at least partially enclose the space.

BRIEF DESCRIPTION OF THE DRAWINGS

The description particularly refers to the accompanying figures in which:

FIG. 5 is a perspective view of a tissue marking system;

FIG. 6 is a top view of another tissue marking system;

FIG. 6a is a sectional view of the tissue marking system of FIG. 6 taken along line A-A of FIG. 6;

Before any embodiments of the invention are explained, it is to be understood that the invention is not limited in its application to the details of construction and the arrangements of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof is meant to encompass the items listed thereafter and equivalence thereof as well as additional items. The terms "connected," "coupled," and "mounted" and variations thereof are used broadly and encompass direct and indirect connections, couplings, and mountings. In addition, the terms "connected" and "coupled" and variations thereof are not restricted to physical or mechanical connections or couplings.

DETAILED DESCRIPTION OF THE INVENTION

Figure 1:
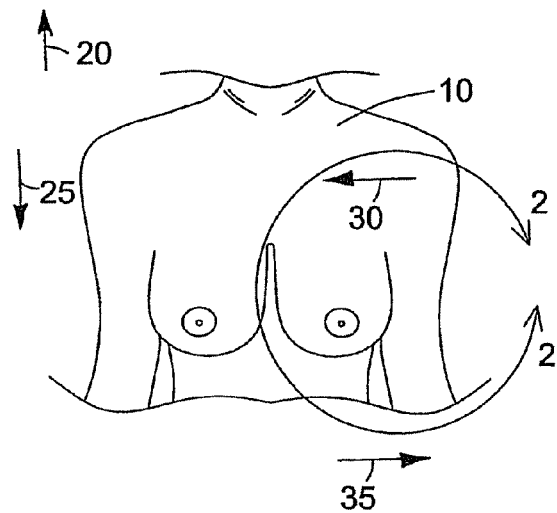
FIG. 1 is a top view of a patient including a tissue sample to be removed from the patient.
Figure 2:
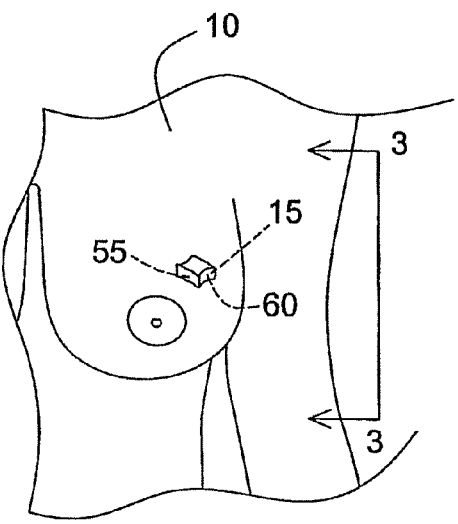
FIG. 2 is an enlarged top view of a portion of the patient and tissue sample of FIG. 1.
Figure 3:
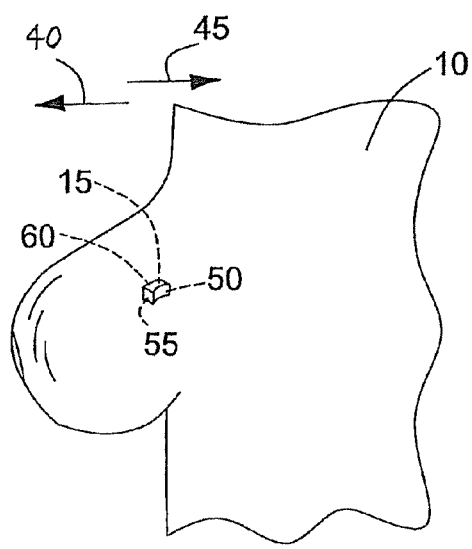
FIG. 3 is a side view of the portion of the patient and tissue sample of FIG. 1.

With reference to FIGS. 1-3, a patient 10 and a tissue sample 15 are illustrated to show the tissue sample's orientation in the patient 10. Before proceeding, it should be noted that the present invention will be described as it relates to a tissue sample 15 removed from a breast. However, one of ordinary skill in the art will realize that the invention is applicable to many other tissue samples in which orientation is important. For example, basal cell carcinoma also requires that a tissue sample be removed, and that its orientation be identified to verify that sufficient margin has been removed. As such, the invention should not be limited only to the uses described herein as it is well suited for use with any tissue that required orientation for pathology. These tissues include but are not limited to samples of breast, bone, thyroid, lymph nodes, brain, sarcomas, kidney, bowel, spleen, soft tissue masses, melanoma, squamous cell skin cancer, basal cell cancer, liver tumors, and the like.

FIG. 1 shows a view looking down on the patient 10. For purposes of description, the direction 20 toward the patient's head will be identified as superior, while the opposite direction 25 is inferior. The direction 30 toward the patient's midline is defined as medial, while the opposite direction 35 is defined as lateral. With reference to FIG. 3, a side view of a portion of the patient is illustrated to further illustrate orientation. The direction 40 toward the patient's exterior is defined as superficial, while the opposite direction 45 is defined as deep.

Figure 4:
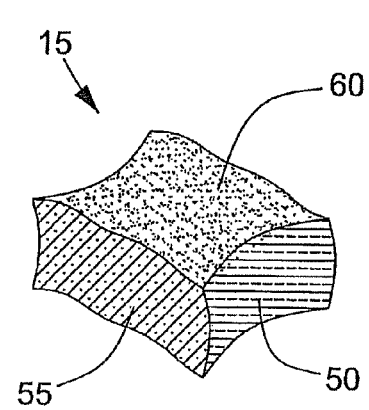
FIG. 4 is a perspective view of the tissue sample of FIG. 1 after being removed from the patient of FIG. 1.

FIGS. 2 and 3 illustrate the tissue sample 15 within the patient 10 prior to its removal, while FIG. 4 shows that same tissue sample 15 after removal. With the sample 15 still in the patient 10, the three surfaces 50, 55, 60 that will be marked can be seen. While any three planes or surfaces of the tissue sample 15 can be used to identify the orientation of the sample 15, it is preferred that at least three substantially orthogonal surfaces be identified, with some applications marking six surfaces. In FIGS. 2 and 3, the lateral surface 50, inferior surface 55, and superficial surface 60 of the tissue sample 15 are shaded differently for illustrative purposes. In FIG. 4, the same three surfaces 50, 55, 60 are shaded to indicate that they have been marked with a different color.

Before proceeding, it should be noted that the term "ink" as used herein is meant to encompass any coloring element that can be applied to a tissue sample 15, with dye, paint, and stains being a few examples. As such, the invention should not be limited to ink alone.

To mark the surfaces 50, 55, 60, three different color inks are employed. FIG. 5 illustrates a container 80 suited for use in marking the tissue sample 15. The container 80 includes a housing 85 that defines three substantially separated compartments 90, 95, 100 and a cover 105 pivotally attached to the housing 85. A perimeter 86 extends around the container 80 and encircles the three compartments 90, 95, 100. Each of the three different color inks is disposed within one of the three compartments 90, 95, 100. The cover 105 is movable between a covering position where it covers the three compartments 90, 95, 100 and cooperates with the housing 85 to completely separate the compartments 90, 95, 100, and an open position where the ink is accessible.

Each compartment 90, 95, 100 includes a bottom surface and a wall that surrounds the bottom surface. Opposite the bottom surface is an opening that allows for access to the ink during use.

In some constructions, each of the inks is simply disposed within one of the compartments 90, 95, 100. Generally, the ink in the compartments is in liquid form. In other constructions, an ink absorbent material 110, such as foam or felt, is disposed within each compartment 90, 95, 100 and is operable to absorb and hold the ink to inhibit spillage and mixing between the ink compartments 90, 95, 100.

Each quantity of ink is a different color than the remaining two quantities of ink. Thus, the first quantity of ink may be yellow, the second quantity of ink may be red, and the third quantity of ink may be black. Of course different colors (e.g., black, blue, green, red, yellow, orange, violet, and the like) could also be employed if desired. In addition, different colors may be employed depending on the particular tissue sample 15 to be removed. For example, breast tissue may be better examined if yellow, red, and blue inks are used, while basal cell samples may be better examined using red, blue, and black ink. Thus, the actual colors employed may be varied greatly.

Generally, the container 80 is a single use tool that is used during a surgical procedure or a series of surgical procedures performed during the course of a day. Thus, the container 80 and its contents are sterilized. While many different sterilization procedures are possible, it is believed that gamma ray sterilization is best suited to the task of sterilizing the container 80 and its contents with other sterilization processes also being possible. In some constructions, a forceps 115 or tweezers is attached to the cover 105 and can be removed for use in grasping and marking the tissue sample 15. Thus, the tissue sample 15 can be marked using the enclosed forceps 115 and the forceps 115 and the container 80 can be discarded after use.

While many different manufacturing processes are possible it is preferred that the container 80, including the cover 105, be injection molded as a single component. In constructions that are molded as a single component, a living hinge 118 would generally be employed between the cover 105 and the housing 85. Of course, other manufacturing methods and other connections between the cover 105 and housing 85 could be employed if desired.

FIG. 6 illustrates another container 120 that supports three ink reservoirs 125, 126, 127 and is suited for use in marking the tissue sample 15. Like the container 80, the container 120 is a single use tool that is used during a surgical procedure or a series of surgical procedures throughout a day. For example, one container could be opened during a first surgical procedure and could be used throughout the day for a series of procedures before being discarded. In preferred constructions, the container 120 and its contents are sterilized before they are opened. The container 120 includes a formed portion 130 that defines the three ink reservoirs 125, 126, 127. The reservoirs 125, 126, 127 are slight depressions in the fanned portion 130 that are sized to contain a quantity of ink. A first isolation space 140 is formed between the first reservoir 125 and the second reservoir 126 and a second isolation space 145 is formed between the second reservoir 126 and the third reservoir 127. The formed portion 130 also defines a perimeter 150 that surrounds the three reservoirs 125, 126, 127. In most constructions, the perimeter 150, the first isolation space 140, and the second isolation space 145 are all substantially disposed within a single plane and the reservoirs 125, 126, 127 extend below that plane.

In some constructions, a ridge 155 (shown in FIG. 6a) is formed around the perimeter 150 to increase the stiffness of the formed portion 130. The ridge 155 may have a semicircular, square, triangular, polygonal, or any other suitable cross-section. Generally, the ridge 155 extends downward below the perimeter to provide the additional stiffness. The ridge 155 also reduces the likelihood of tearing a surgical glove by reducing the number of sharp edges. The increased stiffness that results from the ridge 155 allows the container 120 to be used without being completely supported from beneath the reservoirs 125, 126, 127.

The ink, dye, or other marking substance is disposed within each of the reservoirs 125, 126, 127. As discussed with regard to FIG. 5, an ink absorbing material 160 such as felt or foam, can be placed within each of the reservoirs 125, 126, 127 to hold the ink and reduce the likelihood of spillage and mixing.

A cover 165 extends over the top of the open reservoirs 125, 126, 127 and sealably engages the perimeter 150, the first isolation space 140, and the second isolation space 145. The cover 165 inhibits spillage, mixing, drying, and contamination of the ink before and after sterilization. In most constructions, the cover 165 is a thin plastic film or a thin foil that is adhesively bonded, heat sealed, or otherwise attached to the formed portion 130. In adhesively bonded constructions, an adhesive is applied to the one or both of the cover 165 and the formed portion 130 in, or adjacent to, the perimeter 150, the first isolation space 140, and the second isolation space 145 such that when the cover 165 is positioned as desired, the cover 165 adhesively bonds to the formed portion 130. Once sealed by the cover 165, the container 120 and the ink can be sterilized, transported, and stored for future use.

It should be noted that the thin plastic cover 165 could be used with the construction of FIG. 5 in place of, or in conjunction with, the cover 105.

To manufacture the container 120, the formed portion 130 is first stamped or injection molded from a thermoplastic material. Of course other materials (e.g., metals, composites, and the like) and other manufacturing processes could be used if desired. The ink holding component 160 (e.g., felt, foam, etc.) is positioned within each of the reservoirs 125, 126, 127 if employed. The different color inks are then placed in the individual reservoirs 125, 126, 127. Adhesive is applied to one, or both, of the cover 165 and the formed portion 130 and the cover 165 is positioned on the formed portion 130 to complete the assembly of the container 120. The container 120 is then sterilized and packaged for use at a future date.

Figure 7:
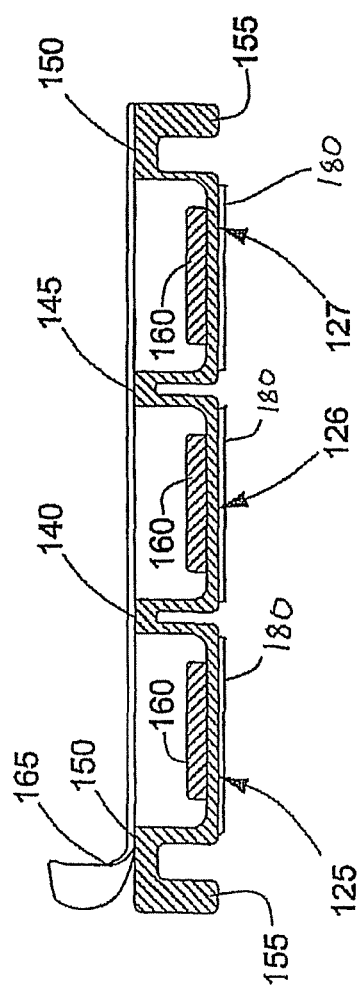
FIG. 7 is a sectional view of the tissue marking system of FIG. 6 taken along line 7-7 of FIG. 6.

FIG. 7 is a sectional view taken along the longitudinal axis of the container 120 of FIG. 6. As can be seen, the perimeter 150 the first isolation space 140 and the second isolation space 145 reside in a single plane that allows the cover to sealably engage the container and seal each reservoir from the other reservoirs. The ridge 155 extends downward to increase the stiffness of the container 120 and to eliminate a thin edge that would otherwise exist and would provide a sharp surface that could tear a surgical glove.

In use, the constructions of FIG. 5 and FIGS. 6, 6a, and 7 function similarly. The cover 105, 165 is first opened or removed to expose the ink. A first surface 50 of the tissue sample 15 is dipped into the first reservoir 90, 125, a second surface 55 of the tissue sample 15 is dipped into the second reservoir 95, 126, and a third surface 60 of the tissue sample 15 is dipped into the third reservoir 100, 127. In most constructions, quick-drying ink is used to further speed the process. Generally, quick-drying ink is ink that dries in less than about 15 minutes with inks that dry in less than 5 minutes being preferred. Once the three surfaces 50, 55, 60 are marked, the orientation of the tissue sample 15 is easily identified and someone other than the surgeon can examine the sample while accurately understanding the original orientation of the tissue within the patient's body.

In some constructions, a label 175 is provided with the container 120 as shown in FIGS. 5 and 6. The label 175 is pre-marked with the ink colors and a space. The nurse or surgeon can identify the surface marked with each color ink by identifying that surface in the space adjacent the correct color on the preprinted label. The label 175 is then pealed off and affixed to the tissue sample 15 or the container that contains the tissue sample 15. In still other constructions, preprinted labels include the colors and a preprinted surface identification, thereby eliminating the need to write the orientation on the label. In addition, some constructions include duplicate labels to allow for easy identification on a patients chart.

It should be noted that all of the constructions illustrated and discussed herein could also include a stick surface 180 (shown in FIGS. 6a and 7). The stick surface reduces the likelihood of the container slipping off of a surface when the container 80, 120 is positioned for use. As such, the stick surface 180 is generally positioned opposite a reservoir opening, as illustrated in FIGS. 6a and 7. Many substances (e.g., rubber, VELCRO, adhesives, and the like) can be used as a stick surface 180.

Figure 8:
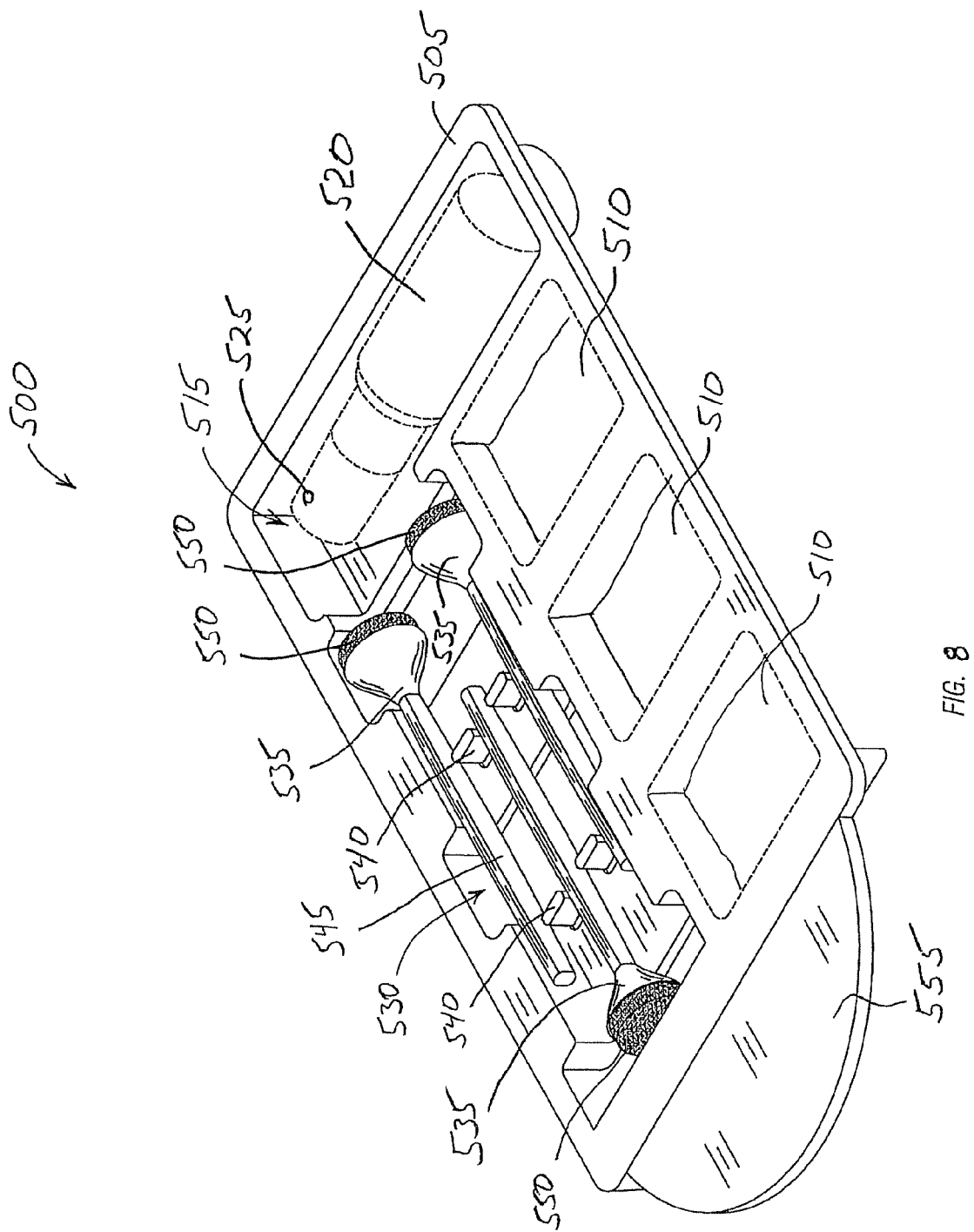
FIG. 8 is a perspective view of another construction of the tissue marking system.

FIG. 8 illustrates another construction of a single-use tissue marking system 500 that includes a container 505 preferably formed from as a single unitary piece using a thermoplastic material. The container 505 defines three reservoirs 510 sized to contain a quantity of ink or die. The container 505 includes another compartment or space 515 sized to receive a container of fixative 520. The fixative 520 can be applied to the tissue sample before or after the ink or die is applied to improve the adhesion of the ink or die and inhibit running and drops. One fixative 520 suitable for use includes vinegar or a vinegar solution, with other fixatives 520 also being possible depending on the type of ink or die employed. In preferred constructions the fixative 520 is contained in a bottle with a spray nozzle 525. The spray nozzle 525 assures that a fine mist of fixative is sprayed onto the tissue rather than large droplets.

The container 505 defines an elongated space 530 that is sized to receive a plurality of applicators 535. In preferred constructions, the quantity of applicators 535 equals the quantity of ink reservoirs 505. As such, the illustrated construction includes three ink reservoirs 505 and three applicators 535. However, other constructions may include a different number of applicators 535 than reservoirs 505. For example, one construction could include six ink reservoirs 505 and three applicators 535. As one of ordinary skill will realize, many different quantities of applicators 535 and reservoirs 505 can be employed. For example, some constructions may include six ink reservoirs 505 and six applicators 535.

In the illustrated construction, the elongated space 530 includes a plurality of separator elements 540 that support and separate the applicators 535 within the space 530. The positioning within the space 530 allows a surgeon or other user to easily remove the applicators 535 with a gloved hand and with little risk of tearing or puncturing the glove.

Each applicator 535 includes a handle portion 545 and a sponge portion 550. In preferred constructions, the handle portion 545 is formed from a plastic material. The sponge portion 550 is sized to absorb and hold a desired quantity of ink, while facilitating the accurate placement of the ink on the tissue sample. By depressing the sponge 550 onto the tissue sample, the surgeon is able to release a desired quantity of ink without causing drips or runs that can blur or confuse the marking.

A removable cover member (not shown) similar to that illustrated in FIGS. 6, 6a, and 7 is employed to cover the container 505. The cover adhesively bonds to the container 505 and seals each ink reservoir 510 from the other ink reservoirs, the fixative space 515, and the elongated space 530 to inhibit leakage of the inks. In preferred constructions, a single one-piece cover is employed to expedite the opening of the ink reservoirs 510 and other spaces 515, 530.

As with the prior embodiments, the container 505 is a single-use device that is preferably sterilized prior to use. The user or surgeon grasps a handle 555 and removes the cover from the container 505 to completely expose each of the inks for use. Each applicator 535 is used with one of the inks to apply the ink to the tissue sample. The fixative 520 is applied before or after the ink is applied to assure that the ink remains fixed to the tissue sample. Once the tissue sample is properly marked, the container 505, cover, and applicators 535 can be discarded.

Figure 9:
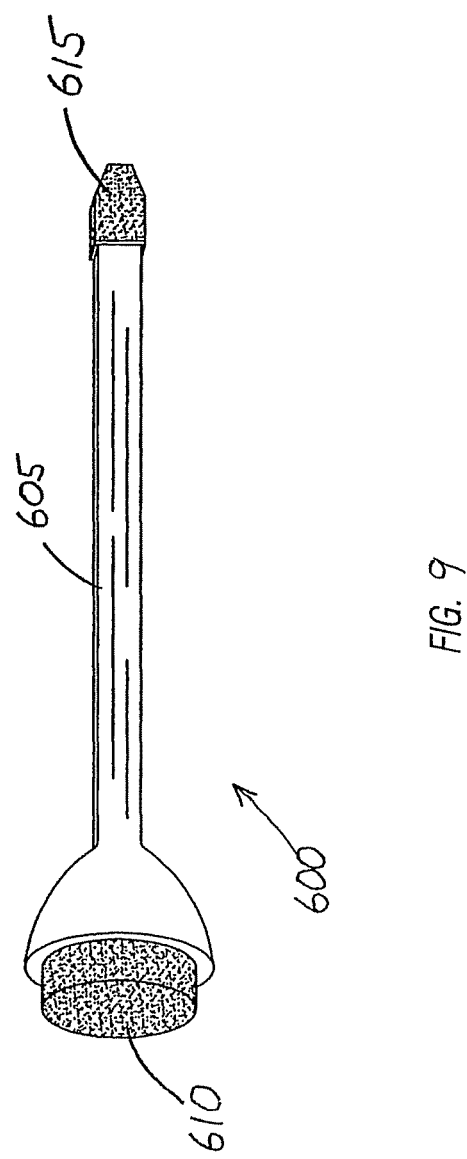
FIG. 9 is a perspective view of an applicator.

As noted, other constructions of the applicator are also possible. As illustrated in FIG. 9, one construction of an applicator 600 includes a handle portion 605, a first sponge portion 610, and a second sponge portion 615. The first sponge portion 610 is similar to the sponge portion 550. The second sponge portion 615 includes a sponge or other material that will hold a quantity of ink. However, the second sponge portion 615 includes a small edge that allows for the finer more accurate placement of ink should it be necessary.

Figure 10:
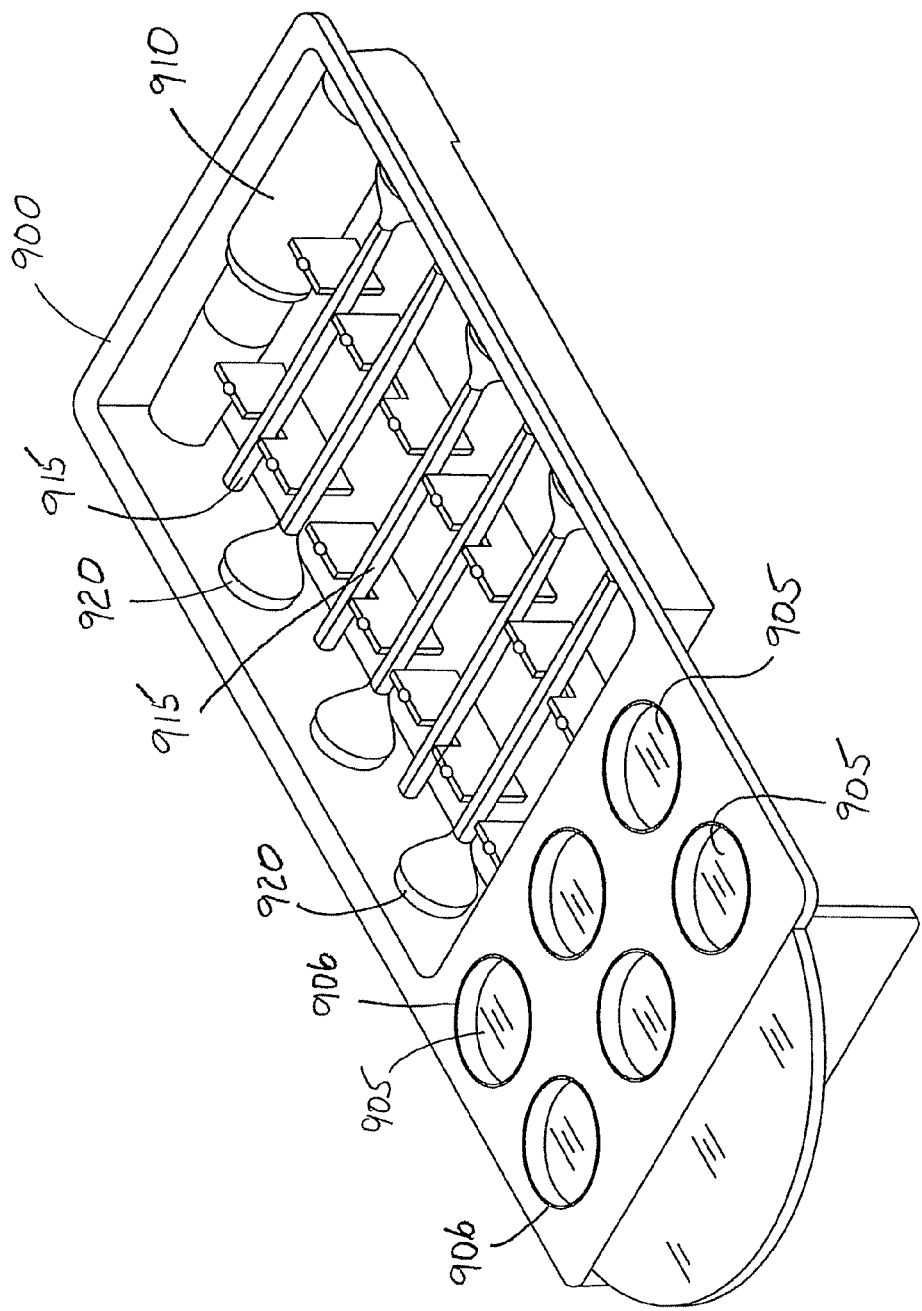
FIG. 10 is a perspective view of another construction of the tissue marking system.

As was also noted, other constructions may employ more reservoirs to hold more colors of ink and may include more applicators. For example, FIG. 10 illustrates a construction that includes a housing 900 that defines six reservoirs 905 that can be filled with six different colors of ink or dye as desired. In some cases, six different color inks are preferred to allow the surgeon to identify all six sides of the tissue sample. Alternatively, preferred colors can be used depending on the type of tissue or tumor.

Each reservoir 905 is surrounded by a ridge 906 that engages a cover (not shown) to assure that when the cover is in place, each reservoir 905 is sealed to inhibit leakage of ink from the reservoir 905.

In some constructions, each of the reservoirs 905 is labeled to aid the surgeon in properly marking the tissue sample. For example, one construction includes one of anterior, posterior, superior, inferior, medial, or lateral adjacent each of the reservoirs 905. Of course other labels could be employed if desired.

The construction of FIG. 10 also includes a bottle of fixative 910 and six applicators 915 rather than the three illustrated in FIG. 8. Each applicator 915 would typically be used with only one color ink to inhibit mixing of colors. While the illustrated applicators 915 include a single sponge end 920, other constructions could employ the applicator 600 illustrated in FIG. 9 if desired.

As with prior constructions, the housing 900 is covered with a single cover (not shown) that seals each of the reservoirs 905 and is removable to expose each of the six reservoirs 905, applicators 915, and fixative 910 for use. Once the cover is removed, the product is used for one or more surgical procedures and then is discarded. Thus, the construction of FIG. 10 is a single-use device.

Although the invention has been described in detail with reference to certain preferred embodiments, variations and modifications exist within the scope and spirit of the invention as described and defined in the following claims.

What is claimed:

1. A method of identifying the orientation of a tissue sample, the method comprising:
   removing a sample of tissue from a patient in an operating room during a single surgical procedure, said sample of tissue having first, second and third surfaces each defined by a tissue margin;
   providing a kit including at least three inks, each of said inks having first, second and third colors, said at least three inks consisting essentially of a composition that causes each of said at least three inks to adhere to the first, second and third surfaces of the tissue sample, respectively, without dripping or running into a crevice of said tissue sample;
   applying the first ink directly onto the first tissue surface;
   applying the second ink directly onto the second tissue surface; and
   applying the third ink directly onto the third tissue surface wherein the ink adheres to the surface of the tissue sample without dripping or running into a crevice of the tissue.

2. The method of claim 1, further comprising sterilizing the first ink, the second ink, and the third ink.

3. The method of claim 2, further comprising providing a housing for said inks, said housing having first, second and third reservoirs; positioning the first ink in the first reservoir; positioning the second ink in the second reservoir; and positioning the third ink in the third reservoir.

4. The method of claim 3, further comprising providing an applicator to hold the first ink and apply it to a surface of the tissue sample.

5. The method of claim 4, wherein first color is yellow, the second color is red, and the third color is black.

6. A method of identifying the orientation of a tissue sample comprising:
   a. excising a tissue sample from a patient during a single surgical procedure in an operating room, the tissue sample having first, second and third surfaces each defined by a tissue margin;
   b. providing a gamma irradiated container including at least three ink reservoirs at least partially defined by the container, each reservoir containing at least three inks each of a different color, said at least three inks consisting essentially of a composition that causes each of said at least three inks to adhere to the first, second and third surfaces of said tissue without dripping or running onto an adjacent tissue margin;
   c. providing a plurality of applicators, each of said plurality of applicators configured to absorb and release a quantity of ink for application to the tissue sample;
   d. applying the first colored ink directly to the first surface of the tissue sample;
   e. applying the second colored ink directly to the second surface of the tissue sample;
   f. applying the third colored ink directly to the third surface of the tissue sample; and
   g. orienting the tissue sample by identifying the marked surface of the tissue sample.

7. The method of claim 6 further comprising discarding said container after a single use or series of uses on a single patient within a single day.

8. The method of claim 6 further comprising subjecting said container to said gamma irradiation for a sufficient time and duration to render said container sufficiently sterile for introduction into a surgical operating room.

9. A method to identify the orientation of a tissue sample excised from a patient comprising:
   a. supplying a container including a quantity of ink reservoirs at least partially defined by the container, each reservoir containing an ink of a different color, said ink being adapted to be applied to an excised tissue surface during a single operating room procedure, said ink further consisting essentially of a composition that causes said ink to adhere to said tissue surface without dripping or running onto an adjacent tissue margin or into a crevice of the tissue sample;
   b. providing instructions with said container to apply a first colored ink to a first surface of a tissue sample having at least first, second and third surfaces;
   d. providing instructions with said container to apply a second colored ink to a second surface of the tissue sample; and
   e. providing instructions with said container to apply a third colored ink to a third surface of the tissue sample.

10. The method of claim 9 wherein said container is configured to be discarded after a single use or series of uses on the same patient within a single day.

11. The method of claim 9 further comprising causing said container to be subjected to gamma irradiation for a sufficient time and duration to render said container sufficiently sterile for introduction into a surgical operating room.

* * * * *